(12) United States Patent
Park et al.

(10) Patent No.: US 7,220,863 B2
(45) Date of Patent: May 22, 2007

(54) PROCESS FOR PREPARING 2-AMINOPYRIDINE DERIVATIVES

(75) Inventors: Tae-Ho Park, Daejeon (KR); Long-Xuan Zhao, Daeryun-si (CN); Sang-Ho Lee, Daejeon (KR)

(73) Assignee: Korea Research Institute of Chemical Technology (KR)

( * ) Notice: Subject to any disclaimer, the term of this patent is extended or adjusted under 35 U.S.C. 154(b) by 121 days.

(21) Appl. No.: 11/209,919

(22) Filed: Aug. 23, 2005

(65) Prior Publication Data

US 2006/0047124 A1  Mar. 2, 2006

(30) Foreign Application Priority Data

Aug. 31, 2004  (KR) ....................... 10-2004-0068822

(51) Int. Cl.
   *C07D 211/72*  (2006.01)

(52) U.S. Cl. ...................................... 546/311; 546/304
(58) Field of Classification Search ................ 546/304, 546/311
   See application file for complete search history.

(56) References Cited

OTHER PUBLICATIONS

Banks et al., N-Halo compounds, Journal of Chemical Society, Perkin Transaction I, 817-821 (1980).*

* cited by examiner

*Primary Examiner*—J. Parsa
(74) *Attorney, Agent, or Firm*—Anderson Kill & Olick, PC

(57) ABSTRACT

A method for preparing 2-aminopyridine derivatives, which comprises substituting of fluorine for hydrazine moiety and reducing with hydrogen using 3-substituted-2,5,6-trifluoropyridine as a starting material, provides 2-aminopyridine derivatives having a purity over 98% under a mild reaction condition.

11 Claims, No Drawings

PROCESS FOR PREPARING 2-AMINOPYRIDINE DERIVATIVES

FIELD OF THE INVENTION

The present invention relates to a method for preparing highly pure 2-aminopyridine derivatives.

DESCRIPTION OF THE PRIOR ART

2-Aminopyridine derivatives having fluorine substituents which are capable of interacting with hydrogen or hydroxy groups as bioisosteres have been known to be bioactive-material intermediates useful for preparation of CCR5 (cellular chemokine receptor 5) modulators or anti-infective agents. Accordingly, there have been numerous attempts to develop an efficient process for preparing such 2-aminopyridine derivatives.

Conventionally, 2-aminopyridine derivatives have been prepared by aminating pyridine having plural fluorine substituents. For example, M. Ma, et al., *J. Chem. Soc. Perkin Transaction I,* 817–821 (1980) discloses a method for preparing 2-amino-3,5,6-trifluoropyridine by heating 2,3,5,6-tetrafluoropyridine at 50° C. in aqueous ammonia under a high pressure, as shown in Reaction Scheme A.

Reaction Scheme A

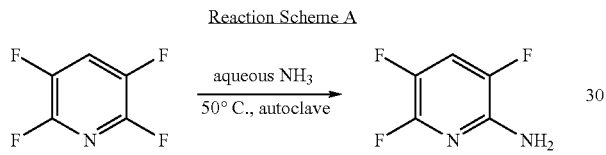

Further, Japanese Laid-open Patent Publication No. 2001-2645 discloses a method for preparing 2,6-diamino-3,5-difluoropyridine by aminating 2,3,5,6-tetrafluoropyridine in aqueous ammonia under a high-temperature and high-pressure condition, as shown in Reaction Scheme B.

Reaction Scheme B

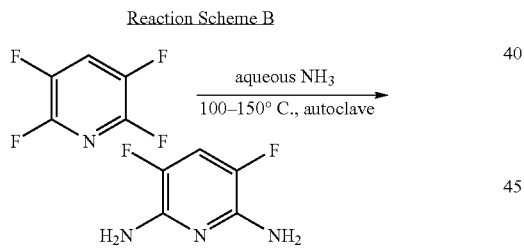

However, such amination methods using aqueous ammonia require a high-temperature and high-pressure condition, and the products obtained thereby have a low purity.

Accordingly, the present inventors have endeavored to develop an improved method for preparing 2-aminopyridine derivatives under a mild condition.

SUMMARY OF THE INVENTION

Accordingly, it is an object of the present invention to provide a mild and efficient method for preparing highly pure 2-aminopyridine derivatives.

In accordance with one aspect of the present invention, there is provided a method for preparing 2-aminopyridine derivatives of formulas (I-a) or (I-b), comprising the steps of: (i) reacting 3-substituted-2,5,6-trifluoropyridine of formula (II) with hydrazine monohydrate to obtain 2-hydrazino-3-substituted-5,6-difluoropyridine of formula (III); and (ii) (a) reducing the compound of formula (III) with hydrogen in the presence of a Raney nickel catalyst to obtain 2-amino-3-substituted-5,6-difluoropyridine of formula (I-a); or (b) dehydrazinating the compound of formula (III) to obtain 5-substituted-2,3-difluoropyridine of formula (IV), reacting the compound of formula (IV) with hydrazine monohydrate to obtain 2-hydrazino-3-fluoro-5-substituted pyridine of formula (V), and reducing the compound of formula (V) with hydrogen in the presence of a Raney nickel catalyst to obtain the compound of formula (I-b):

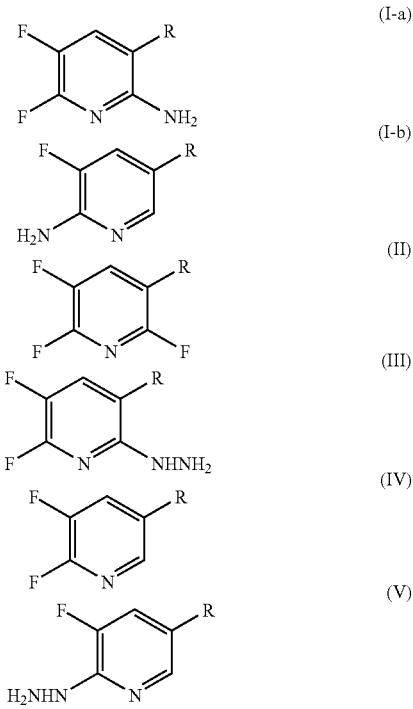

wherein, R is fluorine or chlorine.

DETAILED DESCRIPTION OF THE INVENTION

In the inventive process, the compounds of formulas (I-a) and (I-b) may be prepared as shown in Reaction Scheme 1.

Reaction Scheme 1

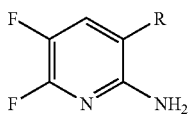

I-a

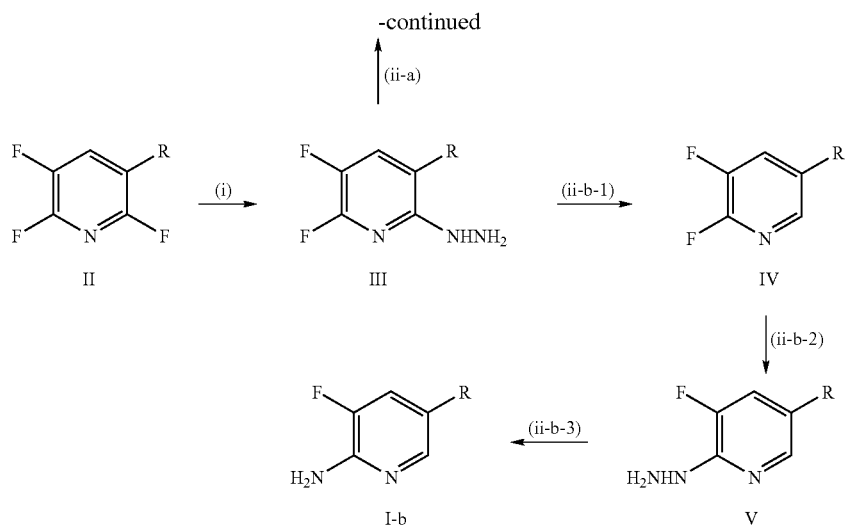

wherein, R have the same meanings as defined above.

In Reaction Scheme 1, the compound of formula (I-a) may be prepared by (i) reacting 3-substituted-2,5,6-trifluoropyridine of formula (II) with hydrazine monohydrate to obtain 2-hydrazino-3-substituted-5,6-difluoropyridine of formula (III), and (ii-a) reducing the compound of formula (III) with hydrogen in the presence of a Raney nickel catalyst.

In step (i), the compound of formula (II), the starting material of the present invention, may be prepared by defluorinating 3-substituted-2,4,5,6-tetrafluoropyridine in an aqueous ammonia in the presence of a zinc catalyst according to a conventional method. The hydrazine monohydrate may be employed in an amount ranging from 3 to 15 equivalents, preferably 3 to 8 equivalents based on the compound of formula (II). Step (i) may be conducted at 50 to 150° C., preferably 30 to 100° C. for 2 to 10 hours, preferably 2 to 8 hours. In step (i), a $C_{1-4}$ alkyl alcohol selected from the group consisting of methanol, ethanol, n-propanol, i-propanol, n-butanol, i-butanol and t-butanol may be used as the solvent, in an amount ranging from 3 to 15 folds, preferably from 3 to 7 folds by weight based on the compound of formula (II).

In step (ii-a), the Raney nickel may be present in an amount ranging from 2 to 15 equivalents, preferably 5 to 12 equivalents based on the compound of formula (III), and a $C_{1-4}$ alkyl alcohol selected from the group including methanol, ethanol, n-propanol, i-propanol, n-butanol, i-butanol and t-butanol may be employed as the solvent in an amount ranging from 20 to 40 folds, preferably 20 to 30 folds by weight based on the compound of formula (III). Step (ii-a) may be carried out at 10 to 35° C., preferably 15 to 25° C. for 10 to 30 hours, preferably 10 to 24 hours.

The compound of formula (I-b) may be prepared by (ii-b-1) dehydrazinating the compound of formula (III) obtained in step (i) to obtain 5-substituted-2,3-difluoropyridine of formula (IV), (ii-b-2) repeating step (i) except for using the compound of formula (IV) instead of the compound of formula (II) to obtain 2-hydrazino-3-fluoro-5-substitutedpyridine of formula (V), and (ii-b-3) repeating step (ii-a) except for using the compound of formula (V) instead of the compound of formula (III).

In step (ii-b-1), the hydrazination may be carried out by reacting the compound of formula (III) with 10% aqueous copper sulfate in an aqueous acetic acid to remove the hydrazino group therefrom. At this time, the acetic acid may be employed in an amount ranging from 10 to 50 folds, preferably from 12 to 30 folds by weight; the water, from 10 to 30 folds, preferably from 12 to 20 folds by weight; and the 10% aqueous copper sulfate, from 50 to 65 folds, preferably from 50 to 60 folds, based on the compound of formula (III). Step (ii-b-1) may be conducted at −10 to 60° C., preferably 0 to 40° C. for 10 to 48 hours, preferably 12 to 40 hours.

In accordance with the inventive method comprising the procedures of substitution of fluorine for a hydrazino group and reduction with hydrogen to introduce amine group, it is possible to prepare 2-aminopyridine derivatives at a high purity over 98% under a mild reaction condition.

The following Examples are given for the purpose of illustration only and are not intended to limit the scope of the invention.

EXAMPLE 1

Preparation of 2-amino-3,5-difluoropyridine

Step 1: Preparation of 2,3,5,6-tetrafluoropyridine 80 g of pentafluoropyridine (Janssen) and 111.5 g of zinc power were added to 560 ml of 20% aqueous ammonia. The resulting mixture was stirred at room temperature for 5 hours, and then gently refluxed to remove water using a Dean-Stark trap, to obtain 60.4 g (yield: 84.5%) of the title compound.

$^1$H-NMR (200 MHz, CDCl$_3$): d 7.53–7.67 (1H, m)

Step 2: Preparation of 2,3,5-trifluoro-6-hydrazinopyridine 23.2 g of the compound obtained in Step 1 and 37.3 ml of hydrazine monohydrate were added to 100 ml of n-propanol, and the resulting mixture was heated to 80° C. for 2 hours. The reaction mixture was distilled under a reduced pressure to remove the solvent. The residue thus obtained was dissolved in 100 ml of chloromethane, washed with water, and dried over anhydrous magnesium sulfate. The dried organic layer was concentrated under a reduced pressure to obtain 21.9 g (yield: 83.8%) of the title compound as a light yellow solid.

¹H-NMR (300 MHz, CDCl₃): d 3.83 (2H, brs), 5.95 (1H, brs), 7.23–7.31 (1H, m)

Step 3: Preparation of 2,3,5-trifluoropyridine 8.2 g of the compound obtained in Step 2 was added to a mixture of 320 ml of acetic acid and 120 ml of water, and 400 ml of 10% aqueous copper sulfate was added thereto. The resulting mixture was refluxed for 24 hours while removing water using a Dean-Stark trap, and the residue was dried to obtain 5.8 g (yield: 87.1%) of the title compound.

¹H-NMR (300 MHz, CDCl₃): d 7.36–7.44 (1H, m), 7.88–7.89 (1H, m)

Step 4: Preparation of 2-hydrazino-3,5-difluoropyridine 6.65 g of the compound obtained in Step 3 and 4.6 ml of hydrazine monohydrate were added to 100 ml of n-propanol. The resulting mixture was refluxed for 6 hours, and distilled under a reduced pressure to remove the solvent. The residue thus obtained was dissolved in 80 ml of chloromethane, washed with water, and dried over anhydrous magnesium sulfate. The resulting organic layer was concentrated under a reduced pressure to obtain 6.20 g (yield: 85.6%) of the title compound.

¹H-NMR (300 MHz, CDCl₃): d 3.75 (2H, brs), 5.90 (1H, brs), 7.06–7.13 (1H, m), 7.91 (1H, s)

Step 5: Preparation of 2-amino-3,5-difluoropyridine

Charged in a hydrogenation reactor were 500 ml of methanol, 14.5 g of the compound obtained in Step 4 and 11.5 g of Raney nickel as a catalyst, and H₂ gas was introduced therein. The reactor was kept at room temperature for 24 hours, and the reaction mixture was filtered through Cellite® to remove the catalyst. The resulting solution was concentrated under a reduced pressure to obtain 10.8 g of the title compound as a light yellow solid (purity: 98.0%).

¹H-NMR (300 MHz, CDCl₃): d 4.52 (2H, brs), 7.07–7.14 (1H, m), 7.81 (1H, d, J=2.4 Hz)

EXAMPLE 2

Preparation of 2-amino-3-fluoro-5-chloropyridine

Step 1: Preparation of 3-chloro-2,5,6-trifluoropyridine 55.5 g of 3-chloro-2,4,5,6-tetrafluoropyridine (Fluorochem) and 20 g of zinc powder were added to 560 ml of 20% aqueous ammonia, and the resulting mixture was stirred at room temperature for 5 hours. The reaction mixture was refluxed while removing water using a Dean-Stark trap, to obtain 46.2 g of the title compound.

¹H-NMR (300 MHz, CDCl₃): d 7.77 (1H, q, J=7.2 Hz)

Step 2: Preparation of 3-chloro-5,6-difluoro-2-hydrazinopyridine 16.6 g of the compound obtained in Step 1 and 20.12 ml of hydrazine monohydrate were added to 100 ml of n-propanol, and the resulting mixture was refluxed 3 hours, and distilled under a reduced pressure to remove the solvent. The residue thus obtained was dissolved in 100 ml of chloromethane, washed with water, and dried over anhydrous magnesium sulfate. The dried organic layer was concentrated under a reduced pressure to obtain 15.9 g (yield: 85.24%) of the title compound.

¹H-NMR (300 MHz, CDCl₃): d 3.80 (2H, brs), 5.91 (1H, brs), 7.53–7.61 (1H, m)

Step 3: Preparation of 3-chloro-5,6-difluoropyridine 17.9 g of the compound obtained in Step 2 was added to a mixture of 360 ml of acetic acid and 135 ml of water, and 450 ml of 10% aqueous copper sulfate was added dropwise thereto. The resulting mixture was refluxed for 24 hours while removing water using a Dean-Stark trap, to obtain 12.9 g of the title compound.

¹H-NMR (300 MHz, CDCl₃): d 7.71–7.78 (1H, m), 8.08–8.10 (1H, m)

Step 4: Preparation of 2-hydrazino-3-fluoro-5-chloropyridine 7.5 g of the compound obtained in Step 3 and 9.57 ml of hydrazine monohydrate were added to 50 ml of n-propanol, the resulting mixture was refluxed for 6 hours, and distilled under a reduced pressure to remove the solvent. The resulting residue was dissolved in 80 ml of chloromethane, washed with water, and dried over anhydrous magnesium sulfate. The dried organic layer was concentrated under a reduced pressure to obtain 7.26 g of the title compound.

¹H-NMR (300 MHz, CDCl₃): d 3.72 (2H, brs), 5.86 (1H, brs), 7.58 (1H, d), 8.41 (1H, s)

Step 5: Preparation of 2-amino-3-fluoro-5-chloropyridine

Charged in a hydrogenation reactor were 100 ml of methanol, 16.1 g of the compound obtained in Step 4 and 8.13 g of Raney nickel catalyst, and H₂ gas was introduced therein. The reactor was kept at room temperature for 12 hours, and the reaction mixture was filtered through Cellite® to remove the catalyst. The filtrate was concentrated under a reduced pressure to obtain 12.7 g of the title compound as a solid (purity: 98.5%).

¹H-NMR (300 MHz, CDCl₃): d 4.45 (2H, brs), 7.57–7.64 (1H, m), 8.30 (1H, s)

EXAMPLE 3

Preparation of 2-amino-3,5,6-trifluoropyridine

Charged in a hydrogenation reactor were 100 ml of methanol, 16.3 g of the compound obtained in Step 2 of Example 1 and 8.0 g of Raney nickel catalyst, and H₂ gas was introduced therein, followed by allowing the reduction to proceed at room temperature for 12 hours. The reaction mixture was filtered through Cellite® to remove the catalyst. The filtrate was concentrated under a reduced pressure to obtain 13.7 g of the title compound as a solid (purity: 99.1%).

¹H-NMR (300 MHz, CDCl₃): d 4.56 (2H, brs), 7.26 (1H, m)

As can be seen from the above, it is possible to prepare 2-aminopyridine derivatives having a purity over 98% under mild reaction conditions according to the inventive method, and thus the inventive method can be advantageously used in various fields including preparation of CCR 5 modulators and anti-infective agents.

While the invention has been described with respect to the specific embodiments, it should be recognized that various modifications and changes may be made by those skilled in the art to the invention which also fall within the scope of the invention as defined by the appended claims.

What is claimed is:

1. A method for preparing a compound of formula (I-a) comprising the steps of (i) reacting a compound of formula (II) with hydrazine monohydrate to obtain a compound of formula (III); and (ii) reducing the compound of formula (III) with hydrogen in the present of a Raney nickel catalyst:

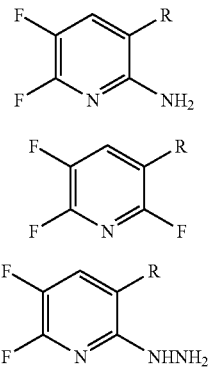

wherein, R is fluorine or chlorine.

2. The method of the claim 1, wherein the hydrazine monohydrate is employed in an amount ranging from 3 to 15 equivalents based on the compound of formula (II) or (IV).

3. The method of the claim 1, wherein the reaction with hydrazino monohydrate is conducted in a $C_{1-4}$ alkyl alcohol solvent at 50 to 150° C.

4. The method of claim 1, wherein the reduction with hydrogen is conducted in a $C_{1-4}$ alkyl alcohol solvent at 10 to 35° C.

5. A method for preparing a compound of formula (I-b) comprising the steps of (i) reacting a compound of formula (II) with hydrazine monohydrate to obtain a compound of formula (III); and (ii) dehydrazinating the compound of formula (III) to obtain a compound of formula (IV), reacting the compound of formula (IV) with hydrazine monohydrate to obtain a compound of formula (V), and reducing the compound of formula (V) with hydrogen in the presence of a Raney nickel catalyst:

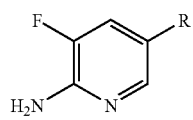

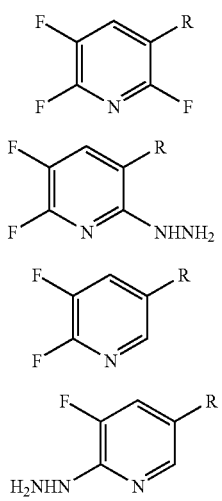

wherein, R is fluorine or chlorine.

6. The method of the claim 5, wherein the hydrazine monohydrate is employed in an amount ranging from 3 to 15 equivalents based on the compound of formula (II) or (IV).

7. The method of the claim 5, wherein the reaction with hydrazino monohydrate is conducted in a $C_{1-4}$ alkyl alcohol solvent at 50 to 150° C.

8. The method of claim 5, wherein the reduction with hydrogen is conducted in a $C_{1-4}$ alkyl alcohol solvent at 10 to 35° C.

9. The method of claim 5, wherein the dehydrazination is carried out by reacting the compound of formula (III) with 10% aqueous copper sulfate in an aqueous acetic acid.

10. The method of claim 9, wherein the acetic acid is employed in an amount ranging from 10 to 50 folds by weight; the water, from 10 to 30 folds by weight; and the 10% aqueous copper sulfate, from 50 to 65 folds by weight, respectively, based on the compound of formula (III).

11. The method of claim 5, wherein the dehydrazination is conducted at −10 to 60° C.

* * * * *